(12) United States Patent
Matsuzaki et al.

(10) Patent No.: US 9,463,058 B2
(45) Date of Patent: Oct. 11, 2016

(54) GUIDE FOR SURGICAL WIRES, METHOD, SYSTEM, AND DEVICE

(71) Applicant: Acumed LLC, Hillsboro, OR (US)

(72) Inventors: Blake A. Matsuzaki, Renton, WA (US); Randall J. Huebner, Portland, OR (US)

(73) Assignee: Acumed LLC, Hillsboro, OR (US)

( * ) Notice: Subject to any disclaimer, the term of this patent is extended or adjusted under 35 U.S.C. 154(b) by 197 days.

(21) Appl. No.: 14/098,250

(22) Filed: Dec. 5, 2013

(65) Prior Publication Data

US 2015/0157379 A1    Jun. 11, 2015

(51) Int. Cl.
*A61B 17/17* (2006.01)
*A61B 17/88* (2006.01)
*A61B 17/90* (2006.01)

(52) U.S. Cl.
CPC ............ *A61B 17/8861* (2013.01); *A61B 17/17* (2013.01); *A61B 17/1796* (2013.01); *A61B 17/88* (2013.01); *A61B 2017/90* (2013.01)

(58) Field of Classification Search
CPC .................. A61B 2017/1782; A61B 17/8861
See application file for complete search history.

(56) References Cited

U.S. PATENT DOCUMENTS

| | | | |
|---|---|---|---|
| 2,531,734 A | 11/1950 | Hopkins | |
| 4,383,527 A | 5/1983 | Asnis et al. | |
| 4,421,112 A | 12/1983 | Mains et al. | |
| 4,952,213 A | 8/1990 | Bowman et al. | |
| 5,246,444 A | 9/1993 | Schreiber | |
| 5,306,278 A | 4/1994 | Dahl et al. | |
| 7,594,917 B2 | 9/2009 | Whittaker et al. | |
| 8,025,667 B2 | 9/2011 | Grant et al. | |
| 8,080,013 B2 | 12/2011 | Whittaker et al. | |
| 8,382,758 B1 | 2/2013 | Sommers | |
| 2004/0102775 A1* | 5/2004 | Huebner | A61B 17/80 606/86 B |
| 2005/0177171 A1 | 8/2005 | Wetzler et al. | |
| 2005/0234469 A1 | 10/2005 | Whittaker et al. | |
| 2006/0149250 A1* | 7/2006 | Castaneda | A61B 17/1728 606/86 B |
| 2012/0253353 A1 | 10/2012 | McBride | |
| 2012/0303033 A1* | 11/2012 | Weiner | A61B 17/151 606/87 |

* cited by examiner

*Primary Examiner* — Nicholas Plionis
(74) *Attorney, Agent, or Firm* — Kolisch Hartwell, P.C.

(57) ABSTRACT

A method and device for improving the placement of a second guide wire in relation to a first guide wire. A body having a first guide wire channel extends from a proximal end to a distal end. The distal end includes a needle-like tip arranged to receive a first guide wire from the first guide wire channel. The body further includes at least one parallel guide wire conduit in close proximity and substantially parallel to the channel. An elongated slot, with a wide opening on the distal end, narrows at the proximal end with a terminus exiting the body in close proximity to the needle-like tip. A second guide wire can be selectively inserted in either the at least one parallel conduit or in the slot to arrange the second guide wire in close and parallel proximity to, or in close and intersecting the trajectory of, the first guide wire.

5 Claims, 5 Drawing Sheets

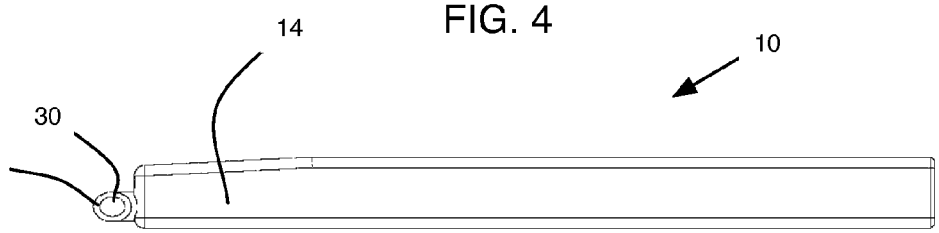
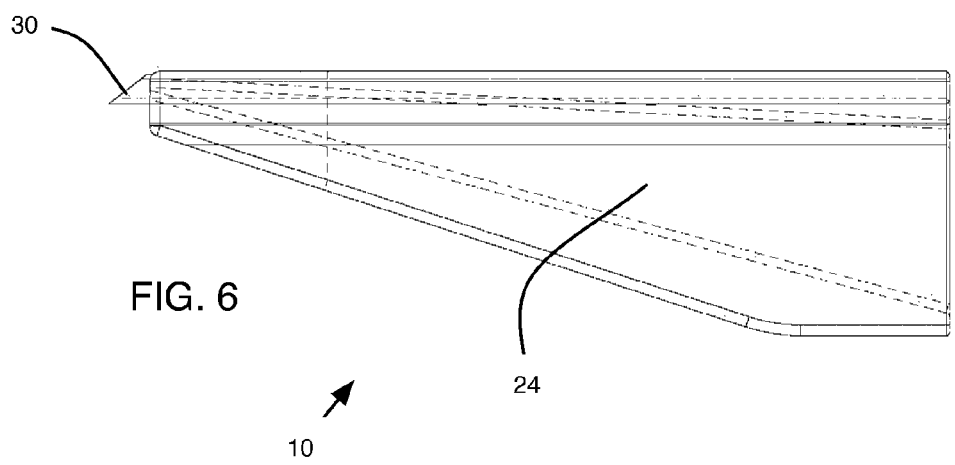

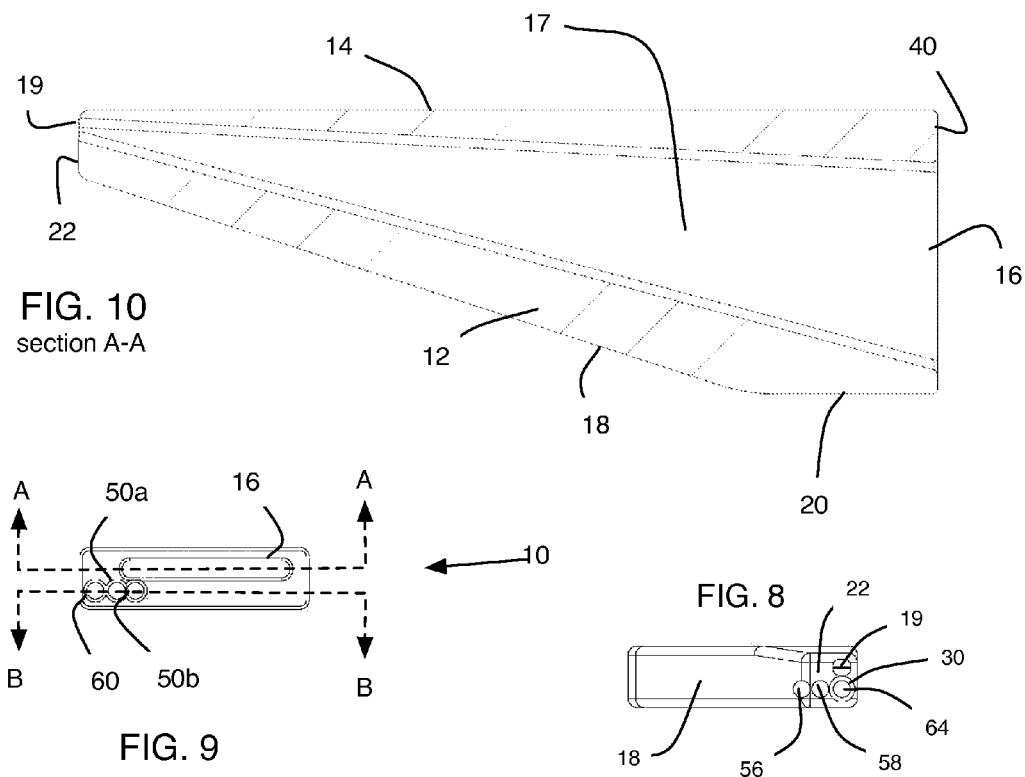
FIG. 10 section A-A
FIG. 9
FIG. 8
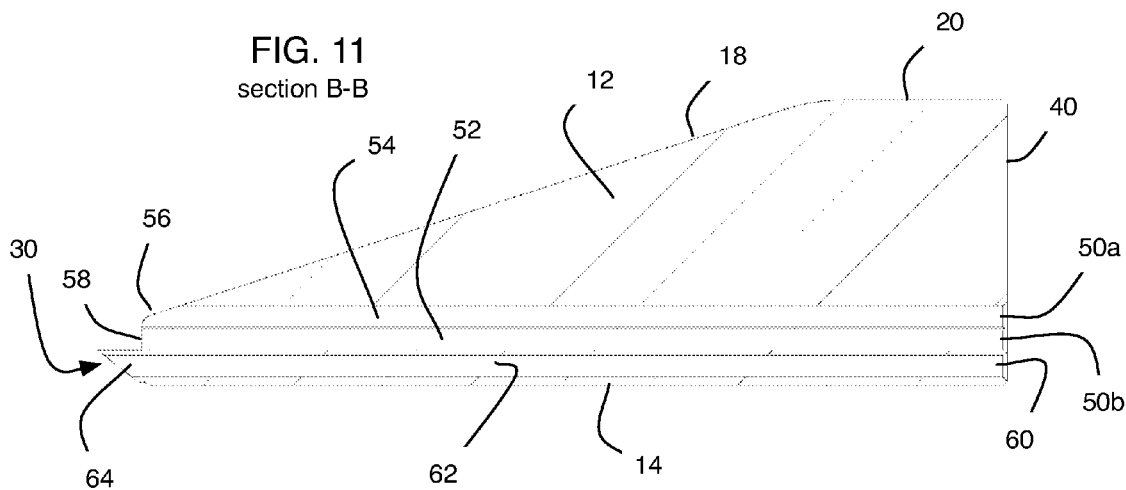
FIG. 11 section B-B

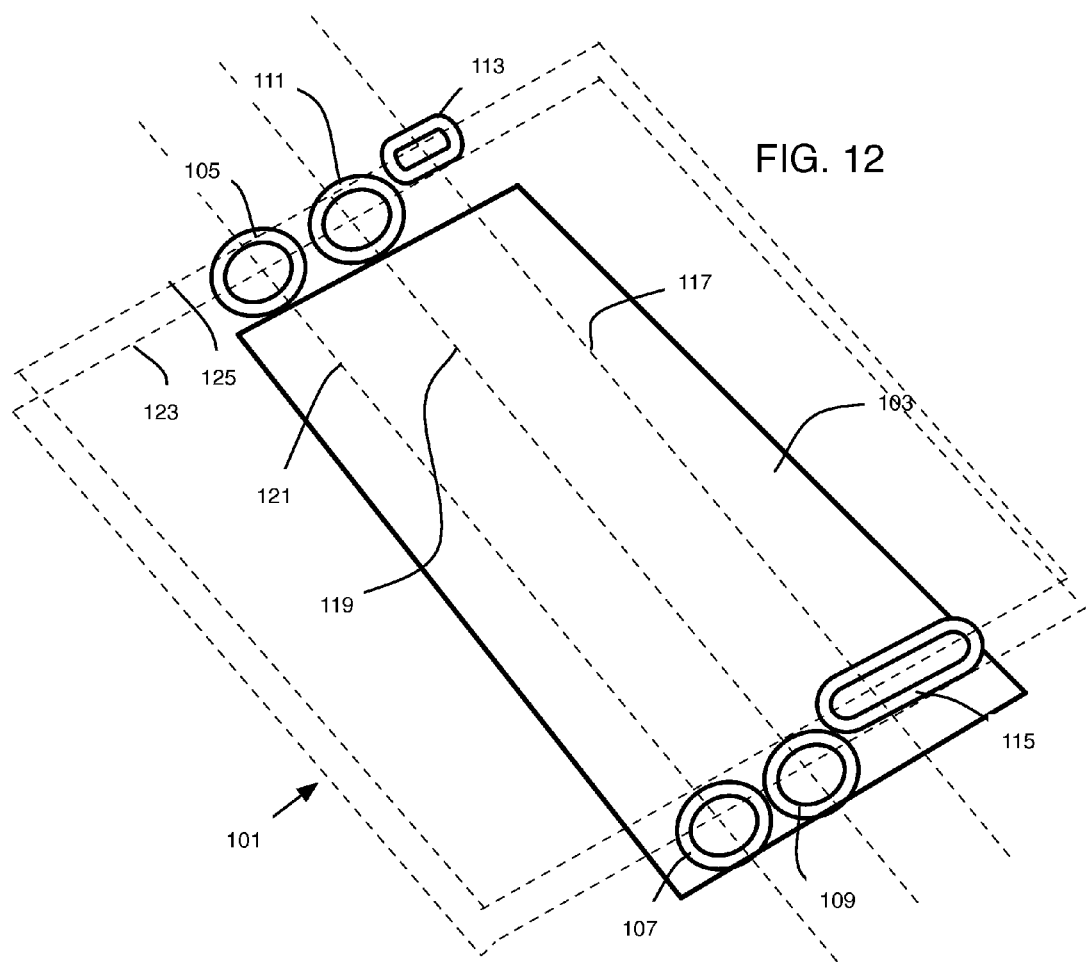

GUIDE FOR SURGICAL WIRES, METHOD, SYSTEM, AND DEVICE

BACKGROUND

The present invention relates to a device and method for treating a fracture in a bone, particularly for treating a wrist fracture. More specifically the present invention relates to devices and methods relating to inserting a first k-wire into bone and then guiding a second k-wire into the bone in parallel or at an angle to the first k-wire within a very narrow space and the invention is well-suited for fractures, fusion, and reduction, for example.

The present invention generally relates to devices used to guide aligning pins, wires, and screws to align bones of the human extremities (upper and lower, for example). More specifically, the present invention relates to devices for axial targeting of scaphoid fractures and the placement of a percutaneous guide wire to correct scapho-lunate instability.

Until recently orthopedic surgeons had inadequate tools to assist in wrist surgeries, particularly related to scapho-lunate instability and non-displaced scaphoid fractures. Prior to that, such repairs to the selected extremity required considerable skill on the part of the surgeon and an even greater amount of guesswork and luck.

When setting fractures, particularly fractures of the hand, the broken or otherwise dislodged bones, typically, are held in a desired alignment with the aid of a Kirshner's wire (K-wire). A common problem with the inserting a K-wire occurs when first inserting the K-wire while also maintaining precise alignment of the arrangement of the bones. This problem also occurs when guiding a drill or placing a cannulated implant. Because of the small diameter of the K-wire (or small diameter of the drill or the size of the cannulated implant, for example) and the limited space between the bones, it was often difficult to determine whether or not the advancing end of the K-wire was aligned, both laterally and vertically, with the carpal bones in the wrist or the elongated metatarsals in the lower extremity. Thus, it is often desired or necessary to place a second K-wire very close to the first K-wire to correct any deficiencies not corrected by the first K-wire. Or, sometimes a second or subsequent K-wire is needed to more precisely align the bones, particularly in the hand, even if the first K-wire was accurately positioned.

One solution to this difficult problem is described by Sommers et al. in U.S. Pat. No. 8,382,758 issued 2013 Feb. 26. Therein, Sommers describes a targeting device that externally clamps to a patient's hand quickly, yet allowing the surgeon to move the patient's hand freely without disrupting the positioning of the targeting guide. Despite the improvement taught by Sommers, there are times when a first guide wire has been placed but the surgeon desires to better align the bones and soft tissue by inserting a second guide wire. Thus, there remains yet a need for another device that enables a surgeon to accurately place a second guide wire based on the position of the first guide wire.

The present invention is directed to overcoming the problems set forth above. It is desirable to have a simple, manually operable device that guides a second wire relative to a first wire that was inserted into an end of a first bone toward an end of a second bone (for example, most indications are axial fixation of one fractured bone, that is scaphoid fractures and Jones Fractures, scapho-lunate instability), while simultaneously aligning the wire so that it is directed in a desired orientation with respect to the first wire. It is also desirable to have a method for pinning two bones together, using the wire insertion guide embodying the present invention, so that the wire is accurately positioned and guided during insertion of the wire through the second bone.

SUMMARY OF THE INVENTION

The present invention improves upon the art and provides an improved device and method for correcting scapho-lunate instability and other similar fractures such as fifth metatarsal (i.e. Jones) fractures, and foot and ankle indications.

Further, the present invention enables a surgeon to more accurately and more precisely insert a second or subsequent k-wire into a bone parallel to and in close proximity to the first wire. This close proximity means as close as possible to the first wire, for example within one k-wire diameter (about 0.045-inches, or less) away from a first k-wire that was previously inserted placed into a bone. Further, the present invention improves guiding a second k-wire to enter a bone as close to one k-wire diameter away from a currently placed wire. Further, the present invention enables an offset insertion of the second k-wire relative to the first k-wire from a variable angle of 0 to 15 degrees with an entry point as close to one k-wire diameter away form currently placed k-wire. And, another feature of the present invention is that a sharp tip helps guide a k-wire into bone by providing a stiff entry point into cartilage and bone.

Some key features of this device include:

1. Needle point to help stabilize the first guide wire by pressing into the cartilage and cortex of the bone, such as the Scaphoid;

2. The device has two or more parallel tunnels (one of which has the needle like tip) these tunnels are very close together thus allowing the surgeon to accurately adjust placement of a second guide wire relative to the first guide wire in very small increments, which is important because a surgeon will often have a very desirable trajectory in the bone with the placement of the first guide wire, but will want to translate the bone ever so slightly with a second guide wire—to date known prior-art methods and devices do not enable precise placement of the second guide wire in very small increments;

3. This device also keeps the starting point of the second guide wire very close to the original wire start point while helping prevent skiving, much the same way the needle stabilized the first wire entry;

4. This device also incorporates a variable angle slot that provides a starting point of the second wire very close to the first wire at a wide range of entry angles that can be determined and adjusted by the surgeon in situ; and 5. Device is predominantly radiolucent so it will enable simultaneous use during imaging by x-rays.

One preferred embodiment of the present invention includes a device and a method. The device includes:

(A) A guide device comprising:
   a substantially flat, elongated rectilinear body comprising
   a top surface,
   a bottom surface opposite the top surface,
   a rectilinear proximal sidewall having a first height and a first width, the proximal sidewall further comprising at least one elongated slot arranged horizontally and at least one parallel-guide-slot holes arranged thereon,
   a rectilinear distal sidewall having the first height and a second width narrower than the first width, the distal sidewall disposed opposite the proximal sidewall,
   a rectilinear left sidewall,
   a first rectilinear right sidewall connected to the proximal sidewall and disposed substantially parallel to the left sidewall and a second rectilinear sidewall connected to the first rectilinear sidewall and configured to angle inward to connect to the distal sidewall, and wherein the proximal sidewall, the distal sidewall, the left sidewall, the first right sidewall and the second right sidewall cooperate to connect the top surface and bottom surface to thereby define a three-dimensional shape having a volume; and a tip extending outward from the distal sidewall, the tip further defining a hollow conduit;

the body further encapsulating a slot extending from the proximal end to the distal end, the slot terminating in an opening adjacent to the tip;

a first guide wire channel extending from the proximal sidewall to the distal sidewall terminating in communication with the tip and whereby the channel configure to slideably receive a first inserted K-wire;

at least one parallel conduit disposed substantially parallel to the channel and configured to extend from the proximal sidewall to the distal sidewall.

And a preferred method includes:

(B) A method for inserting a second guide wire relative to a first guide wire, the method comprising:

providing a guide device for inserting a second guide wire in relation to a first guide wire wherein the device comprises a body configured to enclose a first-wire channel having open ends at a distal and a proximal end of the body, the first-wire channel defining a first plane, at least one second-wire conduit disposed adjacent to and substantially parallel to the first-wire channel, the at least one second-wire conduit having corresponding open ends at the distal and proximal ends of the body and wherein the at least one second-wire conduit is disposed in the first plane, and a slot having a first-width opening at the proximal end and a second-width opening at the distal end, the slot defining a second plane, the second plane configured substantially parallel to the first plane but offset therefrom vertically;

sliding the first guide wire through the first-wire channel;

inserting the second guide wire any any one of the second-wire conduit or the slot.

DRAWING

FIG. 4 is a right side elevation view of the embodiment of FIG. 1.

FIG. 6 is bottom plan view of the embodiment of FIG. 1.

FIG. 8 is another rear elevation view of the embodiment of FIG. 1

FIG. 9 is a front elevation view of FIG. 1 and shows section lines relating to FIGS. 10 and 11.

FIG. 10 is a top cross sectional view along the lines A-A of FIG. 9.

FIG. 11 is a top cross sectional view along the lines of B-B of FIG. 9.

FIG. 12 is a schematic representation of another contemplated embodiment of the present invention.

DESCRIPTION OF THE INVENTION

Figure 1:
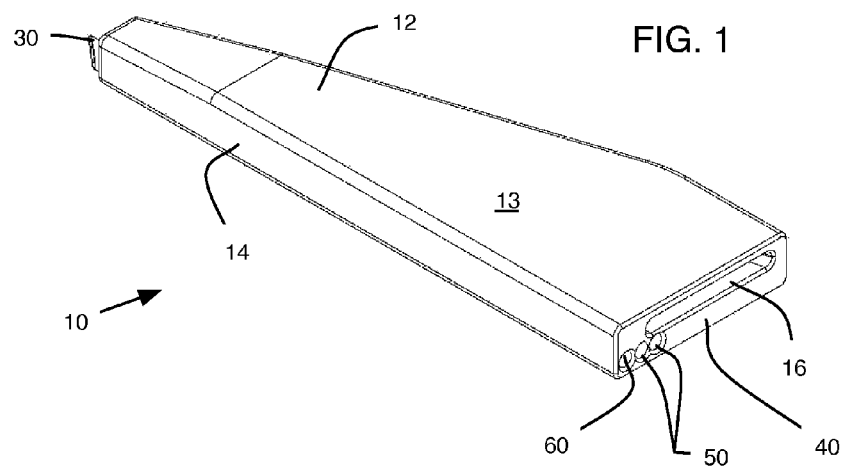
FIG. 1 is an offset frontal view of one embodiment according to the present invention.

Possible preferred embodiments will now be described with reference to the drawings and those skilled in the art will understand that alternative configurations and combinations of components may be substituted without subtracting from the invention. Also, in some figures certain components are omitted to more clearly illustrate the invention.

FIGS. 1-6, and 8-11 illustrate one preferred and contemplated embodiment according to the present invention. As such, a guide device 10 consists of a substantially flat, elongated rectilinear body 12 having a top surface 13, a bottom surface 15 opposite the top surface, and at least one rectilinear proximal sidewall 16 having a first height 27 and a first width 23. The proximal sidewall further includes at least one elongated slot 16 arranged substantially horizontally and a first-wire guide channel hole 60. The guide slot 16 extends through the body 14 and terminates on a distal end 22. This guide slot channel hole 60 is used to receive the first guide wire. In addition, the body 12 includes at least one secondary parallel conduit hole 50 at this proximal end. The parallel conduit hole 50 defines a corresponding channel that extends through the body 12 to terminate at the distal end.

The rectilinear body 12 further includes a substantially rectilinear distal sidewall 22 having the first height 27 and a second width 25 narrower than the first width 23. And, the distal sidewall is disposed opposite the proximal sidewall, as would be understood by those skilled in the art.

Figure 2:
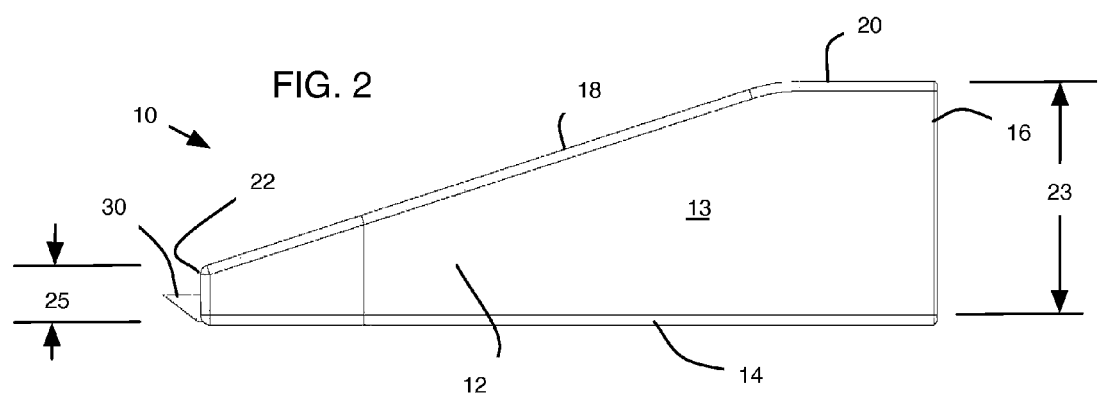
FIG. 2 is a top plan view of the embodiment of FIG. 1.
Figure 3:
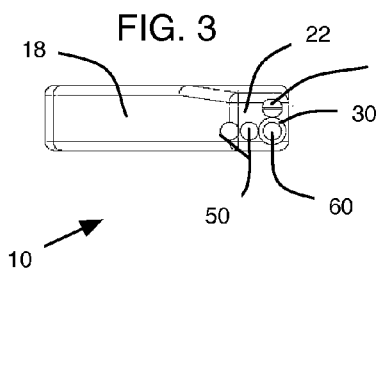
FIG. 3 is a rear elevation view of the embodiment of FIG. 1.
Figure 5:
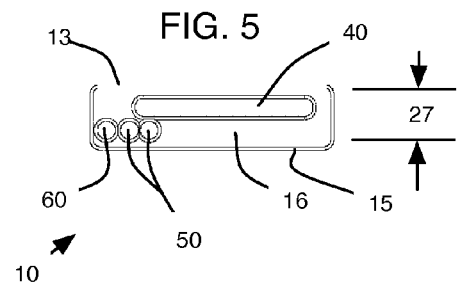
FIG. 5 is a front elevation view of the embodiment of FIG. 1.

Completing the body 12, a rectilinear left sidewall 14 arranges substantially perpendicular to the top 13 and both the proximal 16 and distal 22 sidewalls. Further, a first rectilinear right sidewall 20 connects and otherwise couples to the proximal sidewall 16 and is disposed substantially parallel to the left sidewall 14. A second rectilinear sidewall 18 extends from and is connected and otherwise coupled to the first rectilinear sidewall 20 and configured to angle inward to connect to the distal sidewall 22. FIG. 2 clearly illustrates this relationship of the left and right sidewalls relative to the proximal and distal walls. Accordingly, the proximal sidewall, the distal sidewall, the left sidewall, the first right sidewall and the second right sidewall all cooperate to connect the top surface and bottom surface to thereby define a three-dimensional shape having a volume.

Located at the distal sidewall 22, a (needle-point) tip 30 extends outward from the distal sidewall. The tip 30 further includes a hollow conduit, which enables a connection through the tip for the slot 16 and each guide hole 50 and 60 so that the K-wires can extend through the body 12. This enables the surgeon to slide the first K-wire through the first wire guide conduit hole 60 and then select a second wire and selectively insert it through a second guide wire channel hole 50 or slot 16, thus placing the second wire in close proximity to the first wire. If the surgeon selects the slot, the second wire can be placed at an acute angle relative to the first wire. By selecting a guide channel hole 50, the second wire will be substantially parallel, albeit offset from, the first guide wire.

With specific reference to FIGS. 8-11, the slot 16 and parallel conduits 50 (illustrated as conduit hole 50a and 50b in FIGS. 8-11 to more clearly demonstrate this embodiment) and first-wire channel hole 60 are better illustrated. FIG. 9 is a front view of the device 10 having a slot 16 and a first wire guide channel hole 60 and parallel conduit openings 50a and 50b.

FIG. 10 is a top cross-section of the body 14 and it shows the slot 16 having a substantially trapezoidal passage 17 extending from the proximal end 40 to the distal end 22 with a small opening 19 at the distal end. From this, those skilled in the art will appreciate that a surgeon can insert a second guide wire at any acute or any intersecting angle with the first guide wire.

FIG. 11 is a top cross-section of the body 14 and it shows two parallel (second guide wire) conduit openings 50a and 50b in close proximity to the first wire guide channel hole 60. The first wire guide channel hole 60 includes a first wire channel 62 extending from the proximal end 40 to the distal end 22 at the tip 30 and extending through the body 14 and tip 30 so that a first guide wire can be inserted into a desired location in a patient.

Immediately adjacent to this first guide channel hole 60, a pair of parallel guide conduit openings 50a and 50b also include respective conduits 52 and 54 through the body 14 extending from the proximal end 40 to the distal end 22 and terminating with an exit terminus 56 and 58, respectively, at the distal end so that a second guide wire may be selectively inserted in close proximity to the first guide wire.

This first-wire channel 62 extends from the proximal sidewall to the distal sidewall whereby the first-wire channel is configured to slideably receive a first inserted K-wire. And, at least one second-wire conduit 54 is disposed substantially parallel to the first-wire channel 62 and configured to extend from the proximal sidewall to the distal sidewall whereby the at least a second parallel-channel is further configured to slideably receive a second K-wire and position the second K-wire in substantially close proximity to the first inserted K-wire.

In use, the surgeon will insert the device 10 over a first guide wire (such as a K-wire), which may already be placed in situ by any known means including the method and using the device of Sommers as described in U.S. Pat. No. 8,382,758 issued 2013 Feb. 26, the entire contents of which are incorporated by reference as if set out fully herein. This then leaves conduits 50 or slot 16 available for a second guide wire, which would be inserted by the surgeon in close proximity to the first, either parallel or at an acute angle, as further described below.

Figure 7:
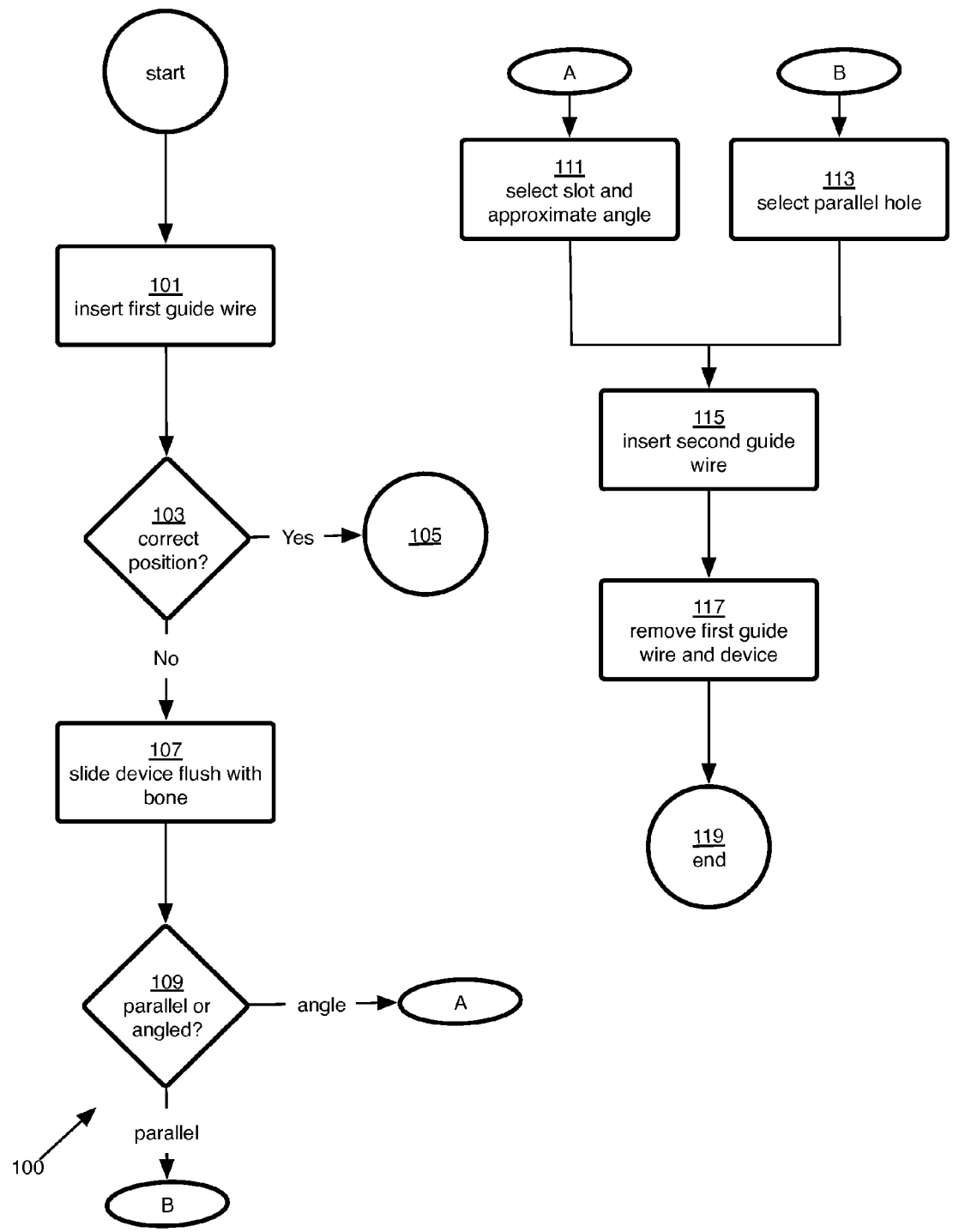
FIG. 7 illustrates a method according to one embodiment of the present invention.

The device 10 is well suited as a Kirschner's-wire (K-wire) guide for surgical placement and securing bone and bone fragments. FIG. 7 illustrates a preferred method 100 using this device 10. Accordingly, the device is used to place a first guide wire and then locate and place a second guide wire from substantially about 3-degrees to substantially about 10-degrees or, alternatively, parallel to, the first guide wire. The user (surgeon) will place a first guide wire conventionally, such as by free hand or with a 14-gauge needle. If the placement of the first wire is not in the surgeon's ideal location the guide device 10 can be used to make small adjustments with respect to the initial (first) wire. Each target hole will exit the end of the guide within 0.060" marked from the center of each wire. This will result in a very similar entry point of the two wires into the bone as long as the tip of the guide is flush with the surface of the bone.

The steps of this first contemplated and preferred method 100 include: First, insert the first guide wire into the bone (block 101). If the surgeon is satisfied (block 103), then there is no need for the device and this method concludes (block 105).

However, if the surgeon decides that fine adjustments to the wire are needed, the surgeon would then slide the device 10 over the first guide wire (using the first-wire guide hole 60) until the device is flush with the bone (block 107). Then, the surgeon decides (block 109) whether to use any one of the parallel, albeit slightly offset, guide conduits (such as 50a or 50b) (block 113), or—alternatively—an angled approach using the slot 16 (block 111).

Next, having selected either the slot 16 for an angled insertion (block 111) or a parallel hole 50 for a parallel albeit slightly offset position (block 113), the surgeon inserts the second guide wire under fluoroscopy (block 115). Finally, the first (initial) guide wire and the guide device 10 are removed (block 117). Now the bone can be manipulated and set in a conventional manner, thus ending this method (block 119).

FIG. 12 is a schematic representation of another contemplated embodiment of the present invention. A guide wire device 101, with structural elements removed from the drawing—those skilled in the art will understand that many alternate structural elements can be arranged on such a device to properly position and arrange the elements as described in the following paragraph.

This contemplated embodiment of the present invention consists of a guide device 101 having a first axis 121. The guide device is well suited for inserting a second guide wire in relation to a first guide wire. The device comprises a body 103 configured to arrange a first-wire axis 121 defined by a first distal ring element 105 axially aligned with a first proximal ring element 107.

Also, at least one second-wire axis 119 arranges adjacent to and substantially parallel to the first-wire axis 121. The at least one second-wire axis defined by a second-wire-distal ring 111 arranged in axial alignment with a second-wire-proximal ring 109 and wherein the at least one second-wire axis is disposed in close proximity to the first-wire axis.

The device also includes a slot 117 defined by a proximal end element 115 in planar alignment with a distal end element 113 to define a plane 125 wherein the plane is configured substantially parallel to the first-wire axis 121 but offset therefrom vertically (see, e.g., guide lines 123 and 125 for vertical offset).

Although the invention has been particularly shown and described with reference to certain embodiments, it will be understood by those skilled in the art that various changes in form and detail may be made without departing from the spirit and scope of the invention.

We claim:

1. A method for inserting a second guide wire relative to a first guide wire, the method comprising:
   providing a guide device comprising a body enclosing a first-wire channel having open ends at a distal end and a proximal end of the body, the first-wire channel defining a first axis arranged in a first horizontal plane, the guide device further enclosing a slot having a first-width opening at the proximal end and a second-width opening at the distal end of the body, wherein the first-width opening is larger than the second-width opening, the slot defining a second horizontal plane substantially parallel to the first horizontal plane but offset therefrom vertically, and further the guide device comprises at least one second-wire conduit disposed adjacent to and substantially parallel to the first axis, the at least one second-wire conduit having corresponding open ends at the distal end and the proximal end of the body, wherein the at least one second-wire conduit defines a second axis disposed parallel to the first axis and arranged in the first horizontal plane; and
   inserting a second guide wire into either the at least one second-wire conduit or the slot.

2. The method of claim 1 further comprising:
inserting a first guide wire in the first-wire channel.

3. A method for inserting a guide wire, the method comprising:
selecting a guide device comprising
a body enclosing a first-wire channel having open ends at a distal end and a proximal end of the body, the first-wire channel defining a first axis arranged in a first horizontal plane,
at least one second-wire conduit arranged along a second axis in the first horizontal plane, the at least one second-wire conduit further being disposed adjacent to and substantially parallel to the first axis, the at least one second-wire conduit having corresponding open ends at the distal end and the proximal end of the body, wherein the second axis is disposed in close proximity to the first axis, and
a slot having a first-width opening at the proximal end and a second-width opening at the distal end, the slot defining a second horizontal plane substantially parallel to the first horizontal plane but offset therefrom vertically, wherein the first-width opening is larger than the second-width opening;
inserting a first guide wire in the first-wire channel; and
inserting a second guide wire in the at least one second-wire conduit.

4. The method of claim 3, wherein the step of selecting a guide device includes a step of selecting a guide device comprising
a tip at the distal end of the body, and wherein the tip is configured to selectively receive the first guide wire from the first-wire channel.

5. The method of claim 3, wherein the step of selecting a guide device includes a step of selecting a guide device in which
the at least one second-wire conduit comprises
a first second-wire conduit disposed in the second horizontal plane, in close proximity to and adjacent to and substantially parallel to the first-wire channel, the first second-wire conduit having corresponding open ends at the distal end and the proximal end of the body, and
a second second-wire conduit disposed in the second horizontal plane, in close proximity to and adjacent to and substantially parallel to the first second-wire conduit, the second second-wire conduit having corresponding open ends at the distal end and the proximal end of the body.

* * * * *